United States Patent [19]

Hope

[11] Plant 4,344

[45] Dec. 12, 1978

[54] KALANCHOE NAMED MONTEZUMA

[75] Inventor: Claude Hope, Cartago, Costa Rica

[73] Assignee: Pan-American Plant Company, West Chicago, Ill.

[21] Appl. No.: 876,461

[22] Filed: Feb. 9, 1978

[51] Int. Cl.[2] ..... A01H 5/00
[52] U.S. Cl. ..... Plt./68
[58] Field of Search ..... Plt./68

*Primary Examiner*—Robert E. Bagwill
*Attorney, Agent, or Firm*—Rummler and Snow

[57] ABSTRACT

A kalanchoe cultivar for greenhouse culture as a potted plant and suitable for year around flowering with photoperiod control, characterized by its intense orange colored florets of medium size which exhibit minimal fading upon aging and which bloom over an extended period due to several weeks of continuous flower bud development. This cultivar is a plant of medium height with an abundance of relatively large glossy foliage at its base, a uniform 10-week response, and a strong resistance to powdery mildew.

1 Drawing Figure

BACKGROUND OF THE NEW PLANT

This new variety of kalanchoe plant originated as a seedling of Red Empress (unpatented) × Swiss Glistening Orange (unpatented) crossed by me in the course of breeding efforts carried on by me at Cartago, Costa Rica, since 1969 with the object of developing new kalanchoe varieties for the commercial market. This plant was selected for reproduction because of its intense orange color and was asexually propagated by me at Cartago, Costa Rica, by means of cuttings from the original plant. Subsequent propagation by vegetative cuttings through successive generations has shown that the distinctive features of the original plant hold true from generation to generation and appear to be firmly fixed.

Present propagation of this new plant is being done at West Chicago, Ill., and at Cortez, Fla., U.S.A.

DESCRIPTION OF THE DRAWING

My new cultivar of kalanchoe plant is illustrated by the accompanying full color photographic drawing which shows a potted plant of the new variety in full bloom, the color rendition being as nearly true as it is reasonably possible to obtain by conventional photographic procedures.

DESCRIPTION OF THE NEW PLANT

The following is a detailed description of this new variety of kalanchoe plant with the color designations according to the R.H.S. Colour Chart published by The Royal Horticultural Society of London, England.

THE PLANT

Origin: Seedling.
Parentage:
- *Seed parent.*—Red Empress (unpatented).
- *Pollen parent.*—Swiss Glistening Orange (unpatented).

Classification:
- *Botanic.*—*Kalanchoe blossfeldiana.*
- *Commercial.*—Kalanchoe pot plant.

Form: Bush.
Height: 20 to 29 cm.
Growth: Upright, sturdy, with medium vigor and very good strength.

Branching: Normal, under natural conditions.
Foliage: Abundant.
- *Leaf size.*—About 6 to 14 cm. long and about 3 to 7 cm. wide.
- *Shape.*—Ovate, with an obtuse tip and dentate margins.
- *Venation.*—Pinnate.
- *Color.*—Upper Side — 146A. Under Side — 146A.
- *Petioles.*—About 13 to 31 mm. long.

THE BUD

Shape: Generally cylindrical with an obtuse tip before opening.
Size:
- *Diameter.*—About 2 mm.
- *Length.*—About 11 to 13 mm.

Rate of opening: Very rapid. The bud opens fully within 1 day.
Sepals: 4 in number, surrounding the receptacle.
- *Length.*—About 6 mm.
- *Width.*—About 1 mm.
- *Appearance.*—Spear-shaped and upstanding.
- *Surface texture.*—Smooth.
- *Surface aspect.*—Shiny.
- *Color.*—Inside — 144A. Outside — 144A.

THE FLOWER

Flowering: 10-week response with photoperiod control and can be flowered the year around.
- *Natural season flowering.*—November through January under Costa Rican conditions.

Blooms: Flower Type — regular and complete.
- *Borne.*—On a compound cyme.
- *Shape.*—Tubular. Petals are flat when bloom is first opened, becoming reflexed as flower matures.
- *Size.*—Medium. Diameter: About 12 to 15 mm. Depth: About 11 to 13 mm.
- *Petals.*—Number — 4 on each flower. Form: Nearly oval, each separate and distinct. Size: Length — About 6 mm. Width — About 5 mm. Texture: Firm. Appearance: Shiny. Color: Upper side — 28A with 17A at the base. Under side — 29B and 31C.
- *Tonality at a distance of 8 feet.*—28B.
- *Discoloration.*—Very little fade after full bloom.

Peduncle: Sturdy and upright.

*Surface texture.*—Smooth.

*Color.*—146C.

Persistence: Flowers hang on and dry.

Effect of weather: None. This variety is recommended only for greenhouse culture.

Disease resistance: This variety exhibits resistance to powdery mildew, as observed in environments where that disease is prevalent.

Fragrance: Typical kalanchoe.

Lasting quality: Approximately 4 weeks.

REPRODUCTIVE ORGANS

Stamens: Eight in number.

*Anthers.*—Color — Brown.

*Filaments.*—Color — Yellow-Green.

*Pollen.*—Color — Yellow.

Pistils: Four in number.

*Stigmas.*—Color — Initially Yellow-Green, turning to Off-White.

Ovaries: Four in number, each developing multiple seeds.

This kalanchoe cultivar is particularly distinguished by its intense orange colored florets which exhibit minimal fading during the blooming period which is extended due to continuous flower bud development over several weeks. The plant is of medium height and has abundant, medium sized, glossy foliage surrounding its base which provides a pleasing green contrast for the bright orange flowers.

I claim:

1. A new and distinct variety of kalanchoe plant, substantially as herein shown and described, characterized by its abundant display of intense orange colored florets appearing on stems of medium height extending from a base of relatively large, glossy green foliage.

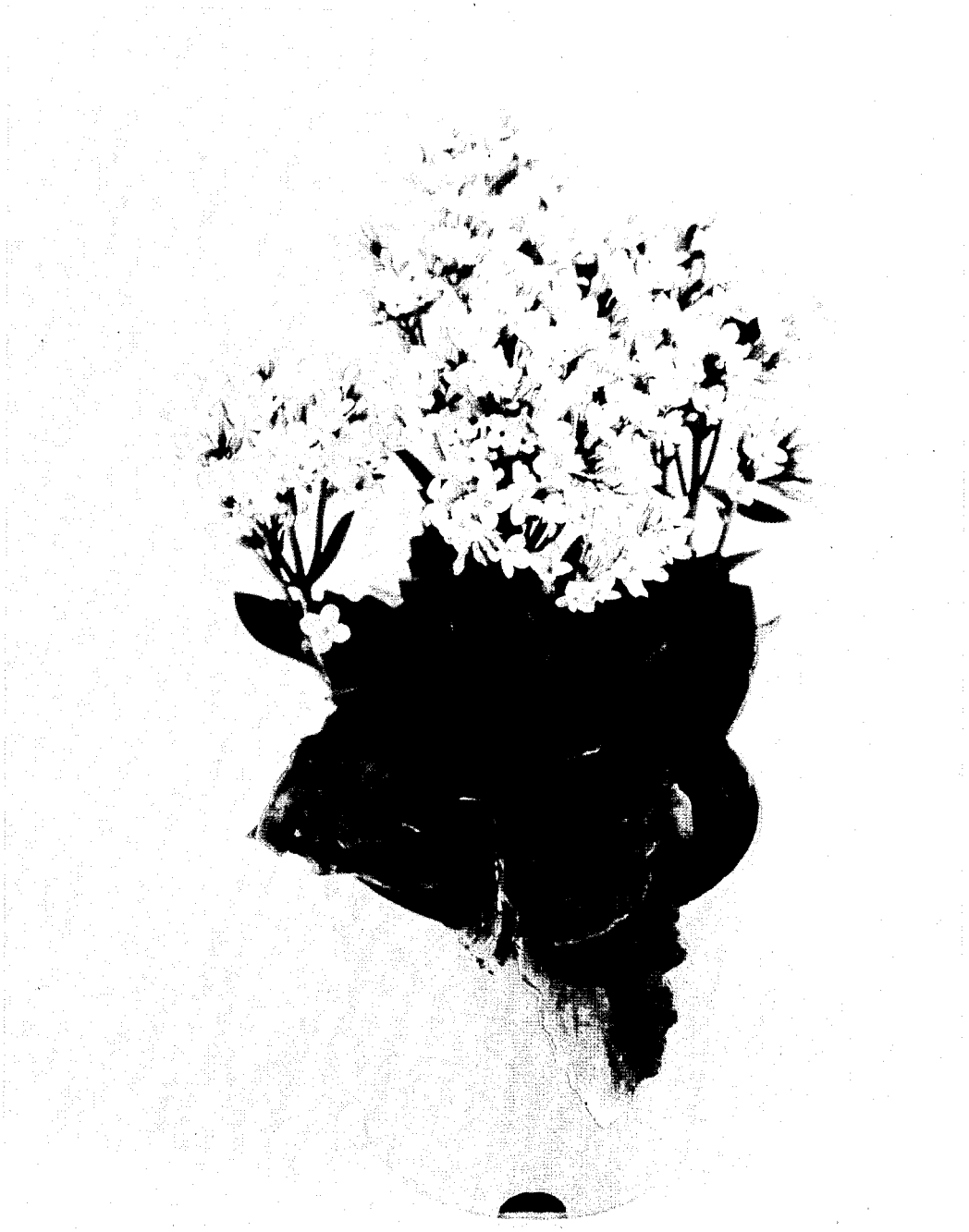

* * * * *